(12) United States Patent
Ricciardi et al.

(10) Patent No.: US 8,074,896 B2
(45) Date of Patent: *Dec. 13, 2011

(54) METHOD AND APPARATUS FOR OPTIMIZING AEROSOL GENERATION WITH ULTRASONIC TRANSDUCERS

(76) Inventors: Jonathan J. Ricciardi, Kennewick, WA (US); Carl L. Ricciardi, Tomahawk, WI (US); Howard J. Swidler, Bethlehem, PA (US); Scott L. Vialpando, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/637,310

(22) Filed: Dec. 14, 2009

(65) Prior Publication Data

US 2010/0090023 A1 Apr. 15, 2010

Related U.S. Application Data

(63) Continuation of application No. 11/509,332, filed on Aug. 24, 2006, now Pat. No. 7,641,130.

(60) Provisional application No. 60/711,858, filed on Aug. 26, 2005.

(51) Int. Cl.
*B05B 17/06* (2006.01)
*B05B 17/04* (2006.01)
*B05B 1/08* (2006.01)

(52) U.S. Cl. .............. 239/102.2; 239/102.1; 128/200.16

(58) Field of Classification Search ........... 239/4, 102.1, 239/102.2; 310/321, 326–328, 334, 340; 128/200.14, 200.16
See application file for complete search history.

(56) References Cited

U.S. PATENT DOCUMENTS

| | | | | | |
|---|---|---|---|---|---|
| 4,523,122 | A | * | 6/1985 | Tone et al. | 310/334 |
| 4,680,499 | A | * | 7/1987 | Umemura et al. | 310/334 |
| 5,166,573 | A | | 11/1992 | Brown | 310/334 |
| 5,355,048 | A | * | 10/1994 | Estes | 310/334 |
| 5,400,665 | A | | 3/1995 | Zhu et al. | 73/863.12 |
| 6,353,277 | B1 | * | 3/2002 | Hahn-Jose | 310/324 |
| 6,782,886 | B2 | | 8/2004 | Narayan et al. | 128/200.14 |
| 2004/0113522 | A1 | * | 6/2004 | Nagahara et al. | 310/326 |
| 2004/0124746 | A1 | * | 7/2004 | Suzuki et al. | 310/326 |
| 2005/0016281 | A1 | * | 1/2005 | Hill | 73/632 |
| 2005/0236932 | A1 | * | 10/2005 | Nagahara et al. | 310/328 |

* cited by examiner

*Primary Examiner* — Darren W Gorman
(74) *Attorney, Agent, or Firm* — Donald J. Ersler

(57) ABSTRACT

The invention is an apparatus and methods for optimizing the performance and protecting one or more aerosol generating transducers from deterioration while operating in a chemically reactive aqueous solution by utilizing one or more protective barrier techniques to eliminate chemical interaction between the aqueous solution and the transducers. The method of the present invention produces an aerosol producing transducer with the transducer housing and assembly to be constructed in such a way as to assure its efficient and effective long-term and problem free operation in an aqueous solution that is chemically reactive.

18 Claims, 4 Drawing Sheets

METHOD AND APPARATUS FOR OPTIMIZING AEROSOL GENERATION WITH ULTRASONIC TRANSDUCERS

CROSS REFERENCE

This application claims priority as a continuation of U.S. Non-Provisional application Ser. No. 11/509,332, now U.S. Pat. No. 7,641,130 which claims priority to U.S. Provisional Application No. 60/711,858 filed on Aug. 26, 2005, each of which is expressly incorporated herein by reference in its entirety, including any references cited therein.

TECHNICAL FIELD OF THE INVENTION

Generally, the present invention relates to an aerosol generating apparatus. More particularly, the present invention relates to an apparatus and methods for protecting and enhancing the aerosol generating apparatus.

BACKGROUND OF THE INVENTION

The apparatus described in U.S. Pat. No. 4,366,125, which is incorporated herein by reference in its entirety, including any references cited therein, generates a hydrogen peroxide mist by an ultrasonic waves vibrator. The mist adheres to the surface of materials being sterilized and is then irradiated with ultraviolet-ray lamps. U.S. Pat. Nos. 5,878,355 and 6,102,992, each of which is incorporated herein by reference in its entirety, including any references cited therein, disclose a method and device for decontamination of a contaminated process area whereby a fine aerosol of an encapsulant is generated to encapsulate contaminants within a contaminated environment. The aerosol is generated by one or more ultrasonic transducers located below the surface of a reservoir containing a liquid. The output of the transducers is focused to either a point and/or directed toward an area near the surface of the liquid to cause a surface disturbance, which results in the formation of an aerosol from the liquid. The transducers used in these apparatuses are made from lead-zirconate-titanate-four (PZT-4) or other piezoelectric materials. This material is coated with a conductive coating (electrode material) that enables an electrical signal to energize the transducer and causes it to emit high frequency pressure (energy).

While operating these prior art apparatuses and similar apparatuses, it has been found that certain liquids, especially acidic solutions, chemically react with the electrode materials of the transducers that generate the aerosol. The result is a noticeable deterioration of both the transducers and their performance. For example, acidic solutions of hydrogen peroxide and peroxyacetic acid have caused noticeable deterioration of the transducers within minutes of operation.

An attempt was made to prevent transducer degradation by coating the face of the transducers with a thin coating of different materials. None of these efforts have been successful. For example, U.S. Pat. No. 4,109,863, which is incorporated herein by reference in its entirety, including any references cited therein, discloses similar findings. The protective coating on the transducer deteriorated to a point where the transducer failed to be energized. It was initially believed that this deterioration was caused by transducer induced cavitation within the tank; however, the aforementioned coatings were also shown to fail in simple immersion tests, conducted over time in an acidic solution, with unpowered transducers. For example, laboratory work indicated that PZT material coated with an electroless nickel plating, or a glaze, were both found to be incompatible with a 4% solution of hydrogen peroxide and peroxyacetic acid, after being exposed to the solution for two weeks at 160.degree. F.

In addition, it was found that various materials used to construct the transducer housing and assembly experienced deterioration after being subjected to a simulated long-term exposure to an acid solution of hydrogen peroxide and peroxyacetic acid. This was observed with an accelerated aging test. This test consisted of placing components constructed of various material types in vessels containing the hydrogen peroxide and peroxyacetic acid solution and subjecting them to increased temperature over a course of time. Without being limited to the theory, this test is based on the theory recognized in the art that at higher temperatures chemical or physical reactions will proceed faster due to the increased probability that two molecules will collide and chemically react.

Without being limited to a mechanism, method, or chemical, it is believed that chemically reactive liquids are necessary in sterilization processes to contact contaminants including but not limited to toxins, bacteria, virus, fungus, and spores (both fungal and bacterial), prions or protein structures, within a target area(s) either killing or neutralizing the bacteria, virus, fungus, and spores, or rendering the toxin, virus, or protein structure incapable of replication or otherwise interfering with the target's cellular physiology, or destroying or neutralizing the toxin. These chemically reactive liquids may be provided as an aerosol. For example, U.S. Pat. No. 4,512,951, which is incorporated herein by reference in its entirety, including any references cited therein, teaches using hydrogen peroxide to sterilize medical articles by condensing hydrogen peroxide-water vapors to deposit a film of liquid on the medical devices. The liquid film is then evaporated off the medical devices.

While the prior art attempted to coat the transducer, there were problems with these coatings. U.S. Pat. Nos. 3,729,138; 4,109,863; and 4,976,259, each of which is incorporated herein by reference in its entirety, including any references cited therein, teach that the optimum thickness of a glass barrier, which may be used as a protective plate and/or cover, on a transducer should be any multiple of one-half (½) the wavelength of the transmitted pressure (energy). The thicknesses of protective barriers have been calculated using wave transmission theories and their respective mathematical formulas known to those skilled in the art. It is estimated that roughly twenty percent (20%) of the energy emitted from the transducers is being transmitted into the liquid beyond the protective barrier. The prior art does not include techniques for further increasing the energy emitted from the transducer with a protective plate and/or cover.

U.S. Pat. Nos. 3,433,461; 3,729,138; 4,109,863; and 4,976,259, each of which is incorporated herein by reference in its entirety, including any references cited therein, teach that an effective thickness of a protective barrier material "interfaced with" a transducer can be any multiple of one-half (½) the wavelength of the transmitted pressure (energy) from the transducer. Prior art has taught that one-half (½) wavelength thick barriers constructed from non-conductive and/or insulating type materials like glass, could be effectively coupled with an ultrasonic transducer for generating aerosol, as long as they included a special design consideration for cooling the transducer, or the transducer was separated from the glass barrier with a layer of liquid. U.S. Pat. No. 3,433,461 teaches utilizing a 1.5 inch diameter transducer bonded to a metal barrier that is a one-half wavelength thick. A problem associated with using metal barriers is corrosion, which was acknowledged in U.S. Pat. No. 3,729,138. In addition, U.S. Pat. No. 3,433,461 discloses that heat has a detrimental effect associated with the operation of a transducer and that a metal barrier interfaced with a transducer permitted the use of much higher driving powers than in prior art devices, since it provided more heat dissipation. Further, the driving power supplied to the transducers is limited by the heat dissipation in the device, which is a function, in each case, of the total area of the generator.

According to U.S. Pat. No. 4,976,259, an attempt was made to bond a glass barrier to a piezoelectric crystal with an adhesive, but such an attempt did not improve on the prior art and resulted in a major loss of acoustic coupling of the ultrasonic energy into the glass cover as the adhesive bond deteriorated. The deterioration was due to high localized temperatures caused by reflected energy resulting from mismatched acoustical impedances.

The prior art does not currently include commercially effective techniques for constructing and operating a high frequency and high power aerosol producing transducer assembly consisting of one or more transducers bonded or adhered to a protective barrier constructed from non-metallic and/or insulative type materials, such as glass, with a thickness that is not one-half (½) of a wavelength. Furthermore, the prior art does not currently include high frequency and high power aerosol producing glass barrier and transducer assemblies that are capable of operating without additional liquid layers or liquid cooling means incorporated into the transducer assembly design.

Therefore, the need for a protective barrier for the aerosol producing transducer that is highly resistant to degradation caused by chemically reactive solutions exists. The protective barrier should withstand the heat generated by a transducer and should function effectively with the transducer to produce a fine aerosol at high output levels (which requires high energy emitted by the transducer). This heat is due to the high frequency and energy that is needed to achieve a high output of aerosolized liquid per hour with the aerosol droplets being less than about 10 microns in size. In general, within the effective frequency band, the higher the power at the effective aerosol producing frequencies, the larger the quantity of aerosol produced; and the higher the effective frequency the smaller the droplet size in the aerosol.

SUMMARY OF THE INVENTION

The apparatus and method of the present invention produces an aerosol producing transducer and its assembly is constructed in such a way as to assure its effective long-term operation and performance while in contact with a chemically reactive aqueous solution, especially acidic solutions.

This invention comprises a method for both protecting and enhancing the performance and/or aerosol production of one or more aerosol generating ultrasonic transducer(s) that operate in contact with any solution, fluid, or liquid (herein collectively "liquid"). The present invention can be used for any application where an aerosol is generated from a transducer and includes, but is not limited to, applications such as sanitization, disinfection, high-level disinfection, sterilization, humidification, fuel aerosolization, as well as the movement, delivery, and/or deposition, of chemical agent(s) or substance(s).

A transducer(s) is protected from chemical interaction with a liquid, as well as any erosion that could be caused by cavitation, by utilizing a protective barrier. In an embodiment, a protective barrier(s) is applied onto the side of the transducer(s) that faces the liquid; where the protective barrier is first heated to a pliable or molten state and then applied to the transducer(s). In another embodiment, a protective barrier(s) is adhered, or bonded to the surface of one or more transducer(s) that faces the liquid. According to an embodiment, the protective barrier may be of any material that has an effective or high chemical resistance to the liquid used. The protective barrier may also be a pane, sheet or plate (herein collectively "plate"), and be made of materials such as glass, ceramic, or a polymer.

In one embodiment, an adhesive, cement, epoxy, or bonding agent/compound, etc. (herein, collectively "adhesive"), whose performance is unaffected and/or not adversely affected by heat, is utilized for adhering, or otherwise connecting a protective barrier with a transducer(s). An interface and/or connection between a protective barrier and a transducer(s) may also be established by other means known to those skilled in the art. Further, no liquid or other medium, other than the adhesive, is necessary between a transducer(s) and a protective barrier for the transducer(s) to function properly.

According to an embodiment of the present invention, a transducer is made from lead-zirconate-titanate-four (PZT-4), or other piezoelectric materials, and it is either interfaced with a reservoir, or mounted to or in a reservoir, or positioned within a reservoir, preferably within a housing or other means to hold, secure, and/or protect the transducer(s), and uses a protective barrier to reduce or eliminate chemical interaction between the liquid and the transducer, as well as physical erosion caused by cavitation. In this embodiment, there is no space between the protective barrier and the transducer, except in the embodiments where adhesives are placed directly in at least a portion of the interface between the transducer and the protective barrier.

One protective barrier application technique is applying a protective barrier onto the surface of the transducer that would be in contact with the liquid absent the protective barrier; where the applied protective barrier is first heated to a pliable or molten state and then applied to the transducer. The thickness of the protective barrier is held to specific tolerances. For a protective barrier, the use of glass is preferred, more preferably quartz glass; however any material that has an effective coefficient of conductivity for pressure (energy) could also be used.

An alternative protective barrier application technique is adhering or interfacing the surface of the transducer(s) that would be in contact with the liquid absent the protective barrier to a protective barrier, preferably a pane, plate, or sheet of glass. The thickness of the protective barrier is held to specific tolerances. For a protective barrier, the use of glass is preferred, more preferably quartz glass; however any material that has an effective coefficient of conductivity for pressure (energy) could also be used.

Another embodiment of the invention comprises operating one or more transducer(s) with one or more protective barrier(s) within a broad operating frequency and broad power range in order to generate aerosol, and further includes utilizing a transducer with a corresponding broad range of resonant frequencies.

Another embodiment of the invention comprises operating the transducer(s) with a protective barrier at a specific operating frequency and power range for maximum efficiency and aerosol output, and further includes utilizing a transducer with a preferred resonant frequency range.

Unless otherwise stated, wavelength (or .lamda.) in this specification refers to the wavelength of pressure (energy) transmitted by the transducer(s), preferably in the form of a wave.

For a protective barrier material, such as quartz glass, that is either applied in a molten state to a transducer and allowed to cool or interfaced as a plate to a transducer, the optimal thickness of the protective barrier is about 0.001 inches to about 0.125 inches, wherein the thickness is not n/2 of a wavelength of sound or pressure (energy) generated by the transducer, wherein n is any integer, at a frequency between about 0.025 MHz to about 10 MHz, preferably between about 0.5 MHz and about 2.5 MHz, and more preferably between about 1.2 MHz and about 2.2 MHz. The excluded thicknesses are calculated as equal to n/2 of the wavelength, (the wavelength is calculated by (speed of sound through the protective barrier material/frequency)). The speed of sound through quartz glass is approximately 5,500 m/s. Once a thickness is selected (wherein the thickness of the protective barrier is not n/2, wherein n is any integer), the protective barrier is manufactured and adhered to the transducer, and a sweep of frequencies is done at a low power to determine the optimal operating frequency.

The enclosing glass plate has a preferred thickness of ¼ the wave length in glass of the transmitted pressure wave generated by the transducer. In a presently preferred embodiment, the glass thickness is 0.036 inch. However, the glass thickness may lie in the range of 0.026 to 0.060 inch. Further, it has been found that the glass barrier thickness may be increased to any odd multiple of ¼ wave length and still operate effectively to provide a high volume small aerosol particle output. The preferred glass barrier material is quartz glass, but borosilicate glass and other suitable glass material may be used.

The present invention provides a protected transducer and method of protecting and enhancing a transducer that is capable of operating at a high energy output transmitted to a liquid without burning and/or damaging the transducer(s) or the adhesive/bonding agent with which it interfaces, or otherwise diminishing the effectiveness of the transducer, while avoiding issues such as, but not limited to, needing to add cooling mechanisms for the transducer(s), reflected energy resulting from mismatched acoustical impedances, or other circumstances known in the art that can degrade output or cause a transducer(s) to fail.

BRIEF DESCRIPTION OF THE DRAWINGS

The process for protecting and enhancing the performance of aerosol generating ultrasonic transducers operating in aqueous environments, is best understood with reference to the following detailed description of the invention and the drawings in which.

DETAILED DESCRIPTION

Figure 1:
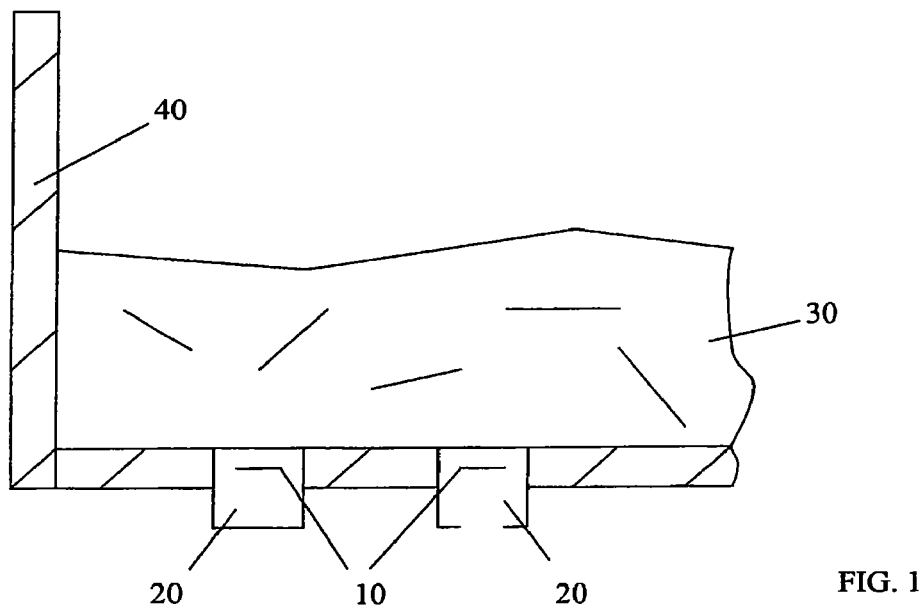
FIG. 1 is a schematic view of an embodiment of a reservoir where one or more aerosol generating ultrasonic transducers are located below the surface of a liquid held within the reservoir.

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

An embodiment of the invention includes a method and apparatus for protecting and enhancing the performance of one or more aerosol generating ultrasonic transducer(s) (10) by adhering one or more protective barrier(s) (60) to a transducer(s) (10). Unless otherwise stated, adhering in this specification includes, but is not limited to adhering, coupling, gluing, attaching, cementing, cohering, fastening, pasting, depositing, applying, melting onto or melting together, and chemically, thermally, or physically bonding. According to an embodiment the transducer(s) (10) may be made of a piezoelectric material, preferably a lead-zirconate-titanate (PZT) material, and more preferably lead-zirconate-titanate-four (PZT-4). According to an embodiment, the protective barrier (60) may be any material that has an effective or high chemical resistance to a liquid (30); however any material that has an effective coefficient of conductivity for pressure (energy) could also be used. Further, the protective barrier (60) may be a pane, sheet, or plate, and may be made of materials such as glass, ceramic, or a polymer. According to an embodiment, the thickness of the protective barrier(s) (60) can range from about 0.001 inches to about 0.125 inches, wherein the thickness is not equal to n/2 of a wavelength of sound or pressure (energy), preferably in the form of a wave, generated by the transducer(s) (10) at a frequency, wherein n is any integer. In an embodiment, the liquid (30) may be, but is not limited to one or more of any chemical, compound, mixture, or substance, which is a liquid, preferably a solution, and may optionally include but is not limited to water, medicines, fertilizers, pesticides, fuels, chemical neutralizers, or anti-pathogen/toxin/fungal/sporicidal agents, substances, combinations thereof, and the like. According to an embodiment, the liquid (30) may also be heated to achieve a desired aerosol (200) output.

According to an embodiment, a protective barrier (60) is adhered to the side of the transducer(s) 10 that faces the liquid (30), preferably hydrogen peroxide and peroxyacetic acid in solution, to separate the transducer(s) (10) from the liquid (30). In an embodiment, the protective barrier (60) is quartz glass and is adhered to the transducer(s) (10) by an adhesive (70) whose performance is unaffected and/or not adversely affected by heat. No liquid or other medium, other than the adhesive (70) (and optionally, a conductive coating (50)), is necessary between the transducer(s) (10) and the protective barrier (60) for the transducer(s) (10) to function properly. According to an embodiment, the thickness of the protective barrier (60) ranges from about 0.001 inches to about 0.125 inches, wherein the thickness is not equal to n/2 of a wavelength of pressure generated by the transducer(s) (10) at a frequency between about 0.025 MHz and about 10 MHz, wherein n is any integer, preferably a thickness between about 0.026 inches and 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz.

Figure 2:
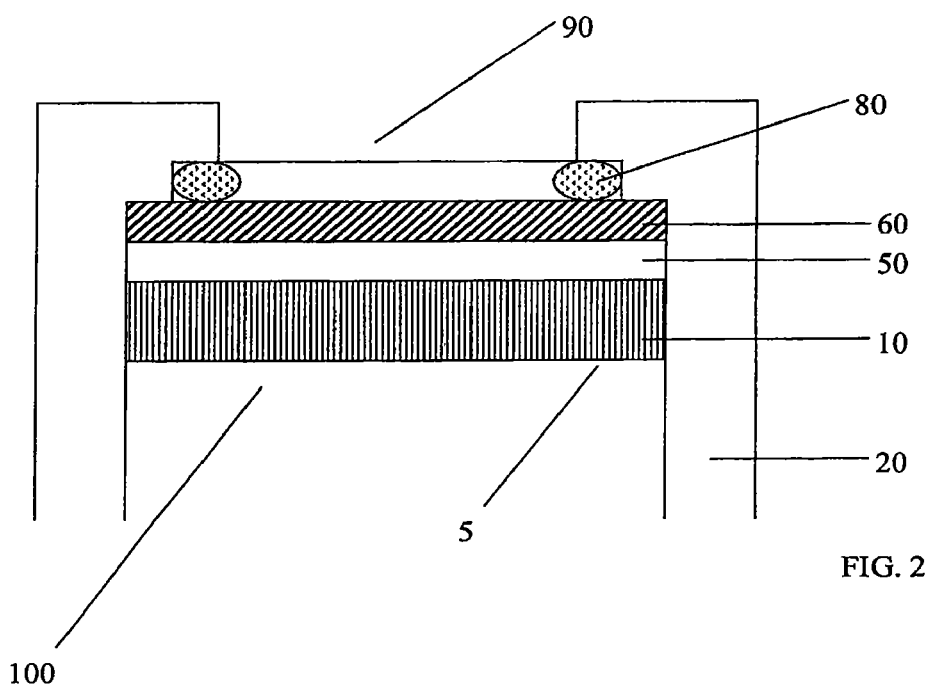
FIG. 2 is a schematic view of an embodiment of a transducer assembly comprising a housing, a transducer, and a protective O-ring seal, wherein a protective barrier is applied to the side of a transducer that faces a liquid.

Referring to FIGS. 1 and 2, an embodiment of the invention includes one or more aerosol generating ultrasonic transducer(s) (10) (and their housings (20), if utilized) located below the surface of a solution, fluid, or liquid (herein collectively "liquid") (30) in a reservoir (40). According to an embodiment, the liquid (30) can be, but is not limited to one or more of any chemical, compound, mixture, or substance, which is a liquid, preferably a solution, and may optionally include but is not limited to water, medicines, fertilizers, pesticides, fuels, chemical neutralizers, or anti-pathogen/toxin/fungal/sporicidal agents, substances, combinations thereof, and the like.

According to a preferred embodiment, a preferred liquid (30) is hydrogen peroxide and peroxyacetic acid in an aqueous solution, which may be effective in sanitization, disinfection, high-level disinfection, and sterilization, and other applications, preferably approximately 2.2% hydrogen peroxide and approximately 0.45% peroxyacetic acid in solution, more preferably approximately 1% hydrogen peroxide and approximately 0.25% peroxyacetic acid in an aqueous solution. Other liquids (30) that may be used include, but are not limited to chlorine dioxide in solution and ozone in solution.

The reservoir (40) may be made of any suitable material that is not affected by the chemical action of the liquid (30). Suitable materials of the housing (40) may include PVC, polypropylene, and stainless steel, but other suitable materials may be used. The aerosol (200) generated by operation of the transducer(s) (10) forms above the surface of the liquid (30) in the reservoir (40) and may be transferred from the reservoir (40) to the space to be treated by a blower (180) or other source of pressurized air, as will be described in greater detail below.

The output of the protected transducer(s) (10) may be focused or directed to a point and/or an area near the surface of the liquid (30) to cause a surface disturbance, which results in the formation of an aerosol (200) of the liquid (30) in the reservoir (40). The aerosol (200) is then blown or otherwise moved with pressurized air, into one or more targeted areas or chambers.

According to an embodiment, the transducer(s) (10) may be made of a piezoelectric material, preferably a lead-zirconate-titanate (PZT) material, and more preferably lead-zirconate-titanate-four (PZT-4). With reference to FIG. 2, the transducer(s) (10) is coated with a conductive coating (50) that enables an electrical signal to energize or drive the transducer(s) (10) causing it to emit pressure (energy) of a desired character. When a protective barrier (60) is adhered or otherwise coupled to a transducer(s) (10) it is understood to mean herein that a conductive coating (50) may exist between the protective barrier (60) and the transducer(s) (10). According to an embodiment, some or all of the conductive coating (50) may be removed from the back of the transducer(s) (10) to allow it to receive the radio frequency (RF) output from the amplifier. Moreover, according to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

According to an embodiment, the transducer(s) (10) may be manufactured into various shapes and sizes according to a desired application, preferably circular in shape. Also, according to an embodiment, the transducer(s) (10) may have a diameter of various lengths, preferably about one (1) inch. By using a protective barrier (60) of the present invention, the transducer(s) (10) may have a smaller diameter and smaller surface area than that taught in the prior art without the problems of overheating and/or failing during operation, the need for a cooling mechanism to prevent the transducer(s) (10) from overheating and/or failing, and/or putting space between the protective barrier (60) and the transducer(s) (10) and/or filling that space with various cooling fluids.

Examples of electronic equipment and methods for operating or driving the transducer(s) (10) are discussed in U.S. Pat. Nos. 5,878,355 and 6,102,992 (both of which are incorporated herein by reference in its entirety, including any references cited therein). U.S. Pat. No. 5,925,966, which is incorporated herein by reference in its entirety, including any references cited therein, also provides details of the hardware necessary to operate the transducer(s) (10). Additional electronic equipment, tolerances, and methods for operating or driving the transducer(s) (10) known in the art may also be used. A variable frequency oscillator or signal generator is used to generate a high frequency wave, preferably a sine or square wave.

According to an embodiment, a preferred oscillator is a digital function generator/counter capable of producing sine, square, triangle, pulse and ramp waves. A preferred oscillator has an adjustable frequency range from about 0.025 MHz to about 12 MHz, and may be set or designed for a particular need or requirement. It preferably has variable output amplitude from 5 mV to 20 Vp-p (Volts peak to peak) being delivered to the amplifier, variable symmetry/duty cycle from 5% to 95% in the ramp or pulse mode, continuous or externally controlled outputs. This signal can then be optionally amplified using a power amplifier to increase the power to the optimum aerosol producing power. The volts peak to peak is a measure of power that is supplied to the transducer(s) (10). A direct current (D.C.) offset between −10 v to +10 v can be added to any of the output waveforms.

In one embodiment, the amplifier is a solid-state amplifier that provides up to 2500 watts of linear power with low harmonic and intermodulation distortion and peak to peak voltages of about 20 volts to about 300 volts; however the number of watts could also be increased in order to provide enough power to drive a desired number of transducers, preferably approximately 100 watts of linear power per transducer(s) (10) with about 190 to about 230 Vp-p.

The amplified signal from the amplifier is used to operate or drive one or a plurality of transducer(s) (10), where in an embodiment each transducer(s) (10) is operated at a frequency range between about 0.025 MHz to about 10 MHz or higher, preferably between about 0.5 MHz to about 2.5 MHz, more preferably between about 1.2 MHz and about 2.2 MHz. Moreover, in such an embodiment each transducer(s) (10) has a resonant frequency between about 0.025 and about 10.0 MHz or higher. The operating frequency is the frequency at which the transducer(s) (10) is being driven or operated. The resonant frequency is the frequency of the transducer(s) (10), unloaded in air, without being adhered to the protective barrier (60) or other parts of the transducer assembly (100).

Optionally, in one embodiment, the conductive coating (50) may be applied to the entirety of the surface of each transducer(s) (10) so that it can be energized. According to an embodiment, some or all of the conductive coating (50) may be removed from the side (5) that faces away from the liquid

(30) in the reservoir (40). The side (5) of the transducer(s) (10) is also the side that receives the radio frequency (RF) output from the amplifier. According to an embodiment, an electrically conductive material (i.e., metal wire, conductive tab or spring, etc.) interfaces or is connected to the conductive coating (50) on the transducer(s) (10), and is then either electrically grounded or electrically connected back to the power amplifier to complete the circuit. This circuit is not polarity sensitive. The electrically conductive material can be attached in their reverse manner.

The transducer(s) (10) is protected from chemical interaction with a liquid (30), as well as any erosion that could be caused by cavitation, by utilizing a protective barrier (60). In an embodiment, referring to FIG. 2, applying a protective barrier (60) onto the side of the transducer(s) (10) that faces the liquid (30); where the protective barrier (60) is first heated to a pliable or molten state and then applied to the transducer(s) (10). In another embodiment, referring to FIG. 3, adhering, or bonding the surface of one or more transducer(s) (10) that faces the liquid (30) with a protective barrier (60). According to an embodiment, the protective barrier (60) may be a pane or plate, and/or be made of materials such as glass, ceramic, or a polymer. Preferably the protective barrier (60) is a sheet of quartz glass. The material of a protective barrier (60) should have an effective or high chemical resistance to the liquid (30) used. The thickness of a protective barrier (60) is held to specific tolerances. In one embodiment, an adhesive, cement, epoxy, or bonding agent/compound, etc. (herein, collectively "adhesive" (70)), whose performance is unaffected and/or not adversely affected by heat, is utilized for adhering, or otherwise connecting a protective barrier (60) with a transducer(s) (10). An interface and/or connection between a protective barrier (60) and a transducer(s) (10) may also be established by other means known to those skilled in the art. Further, no liquid or other medium, other than the adhesive (70) (and optionally, a conductive coating (50)), is necessary between a transducer(s) (10) and a protective barrier (60) for the transducer(s) (10) to function properly. According to an embodiment, glass was chosen due to attributes including, but not limited to its physical and/or mechanical properties, and ability to withstand the heat generated by a transducer(s) (10) and its general ability to withstand chemical attack. The technique of adhering a transducer to a glass barrier material is taught in U.S. Pat. Nos. 4,109,863; 3,433,461; 3,729,138; and 4,976,259, each of which is incorporated herein by reference in its entirety, including the references cited therein.

According to a preferred embodiment, a transducer(s) (10) and/or a transducer assembly (100) are placed in a chemically resistant housing (20) or other chemically resistant means to hold, holdfast, secure, and/or protect the transducer(s) (10). Certain metals and plastics have demonstrated high chemical resistance to various liquids. A chemical resistant seal material or O-ring (herein "O-ring") (80) serves as a seal between the transducer assembly (100), and the liquid (30) in the reservoir (40). According to an embodiment, the O-ring (80) may be made of any chemically resistant material depending upon the composition of the liquid (30) utilized, preferably Viton®. The preferred material has the highest chemical resistance to the liquid used.

In each of the embodiments shown in FIGS. 2-5, the transducer assembly (100), including the transducer(s) (10) and the protective barrier (60), is enclosed or packaged in, assembled with, or coupled with, a housing (20). According to an embodiment, the housing (20) may be a hermetically or non-hermetically sealed or unsealed housing, or other hermetically or non-hermetically sealed or unsealed means to hold, holdfast, secure, and/or protect transducer(s) 10, that is either interfaced with the reservoir (40), or mounted to or in the reservoir (40), or positioned within the reservoir (40), or preferably coupled or attached to the bottom wall of the reservoir (40). According to an embodiment, a sealed interface exists between the protective barrier (60) and/or the housing (20) or means to hold, holdfast, secure, and/or protect the transducer(s) (10).

Figure 3:
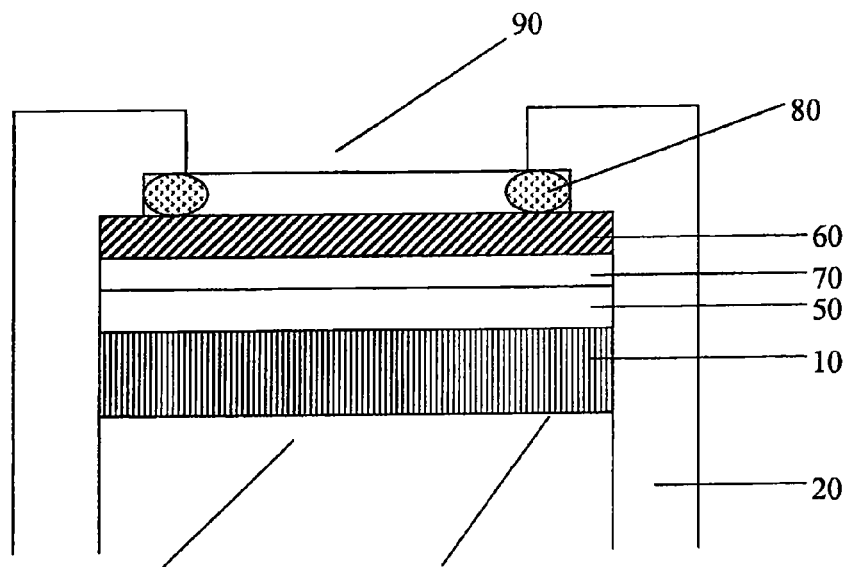
FIG. 3 is a schematic view of an embodiment of a transducer assembly comprising a housing, a transducer coupled with a protective barrier such as a pane, plate, or sheet of glass or other material, and a protective seal above the protective barrier.
Figure 4:
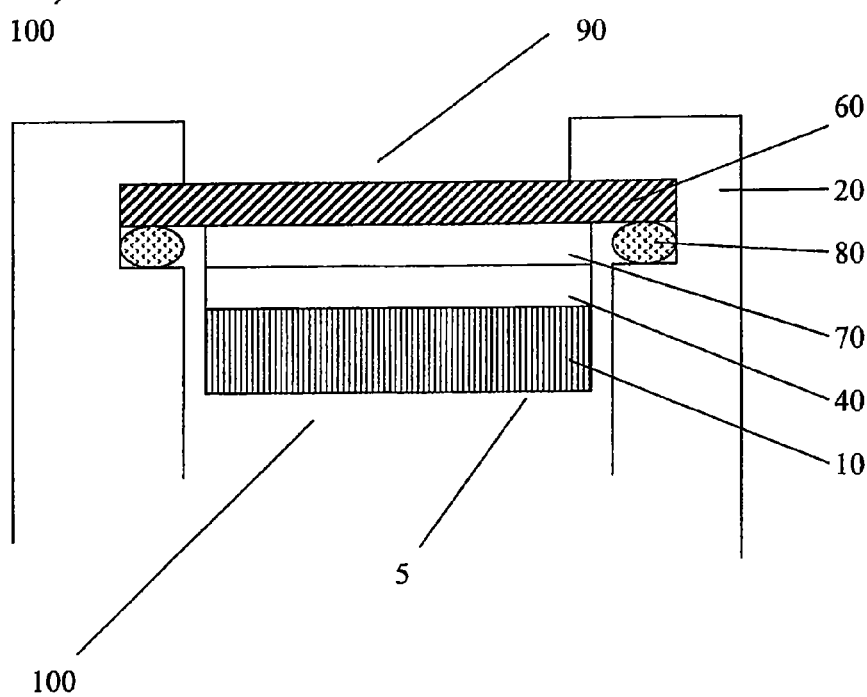
FIG. 4 is a schematic view of an embodiment of a transducer assembly comprising a housing, a transducer coupled with a protective barrier, and a protective seal below the protective barrier.

In one embodiment, see FIGS. 2 and 3, the O-ring seal (80) seals the interface between the protective barrier (60) and the open upper end (90) of the housing (20). In FIG. 4, the O-ring seal (80) is positioned below the protective barrier (60).

Figure 5A:
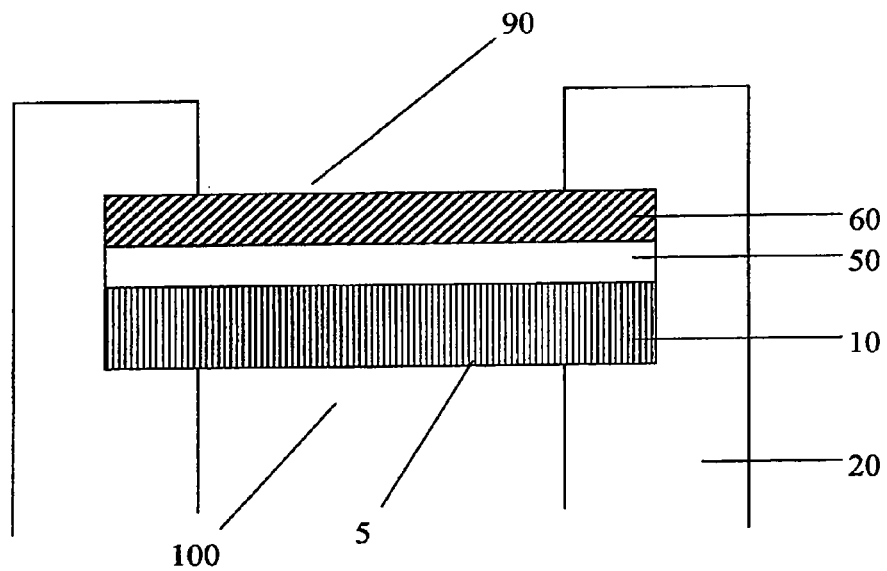
FIGS. 5a and b are a schematic views of embodiments of a transducer assembly according to the present invention.
Figure 5B:
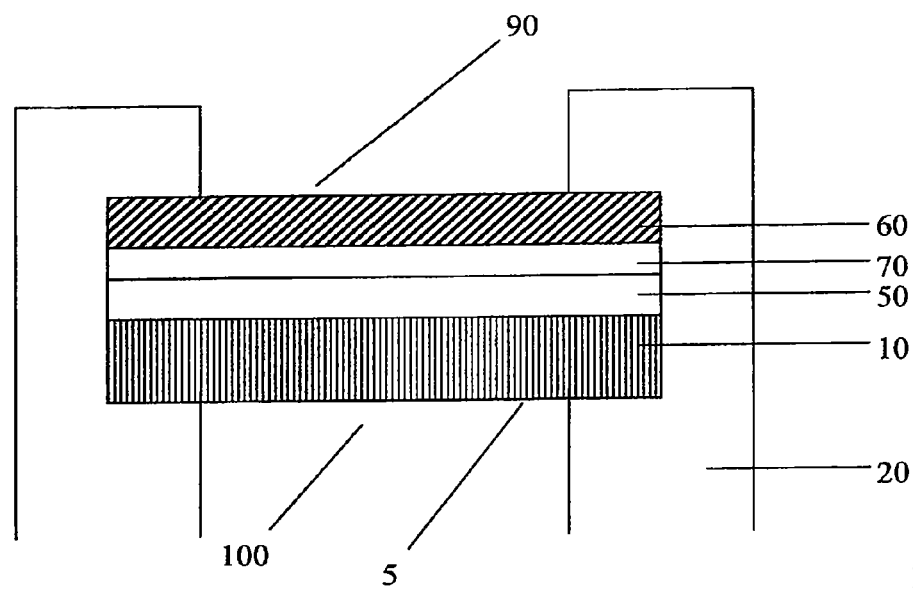

In FIGS. 5a and 5b, the transducer(s) 10 and the protective barrier (60), where the protective barrier (60) is formed and/or assembled by method (1) or (2), is molded, thermoformed, cemented, adhered, or otherwise interfaced with/to the reservoir (40), or the housing (20) or other means to hold, holdfast, secure, and/or protect the transducer(s) (10), which establishes an effective seal between the interfacing materials. Other methods known in the art can also be used to establish this interface. In an another embodiment, the surfaces within the reservoir (40), or other surfaces to which the transducer assembly (100) is coupled, interfaced, connected, or mounted, may also act or function as the housing (20) and FIGS. 2-4 are also applicable in this capacity. Finally, a sealed interface may also exist between the housing (20) or the means to hold, holdfast, secure, and/or protect the transducer(s) (10), and a wall of the reservoir (40), or other surface(s) with which it interfaces.

According to an embodiment, it is preferred that with both protective barrier (60) methods (1) and (2), when glass is used, the glass type used may be of any acid and/or alkaline resistant glass such as, for example, quartz, or Type I (borosilicate glass or Pyrex) or Type II glass as defined by the United States Pharmacopoeia. The protective barrier (60) may be any chemically resistant material. Preferably, the protective barrier (60) has a high chemical resistance to the liquid (30) used.

The selection of a material for either of the two protective barrier (60) assemblies and methods is further determined by the material's impedance properties according to known wave transmission theories. In other words, some materials are better at transmitting pressure (energy) than others. This correlates directly with the efficiency and effectiveness of the transducer(s) (10) and is represented by the maximum amount of aerosol (200) generated by the aerosol generating system (110) per unit of time. In order to maximize the energy transfer into the liquid (30), transmission coefficients for various protective barrier (60) materials are calculated by means of known mathematical formulas pertaining to the various theories of wave transmission known to those of skill in the art. The transmission coefficients are calculated and then compared and the highest transmission coefficient is chosen. Generally, the higher the energy transmitted through the protective barrier (60), the higher the aerosol (200) output. In addition, the higher the frequency, the smaller the particles. According to an embodiment, good wave transmission is achieved through the use of a quartz glass or a borosilicate glass protective barrier (60).

The thickness of the material of the protective barrier (60) is another factor that influences the efficiency and effectiveness of the transducer(s) (10) or the total amount of or size of aerosol (200) the transducer(s) (10) is able to generate. This relates to the fact that operational frequencies will dictate selected glass thicknesses, thinner glass being selected with higher frequencies. These higher operational frequencies produce smaller droplet sizes. In the first protective barrier method, the protective barrier (60) is either formed or applied to the proper thickness. If the thickness of the protective barrier (60) is not within specifications, the protective barrier (60) may be further processed or machined to achieve the proper thickness. The second protective barrier method involves adhering, or otherwise connecting the protective barrier (60), which may be processed or machined to the proper thickness, with the transducer(s) (10). In both methods, the thickness of the protective barrier (60) is controlled to tight tolerances in order to control its transmission coefficient.

It was thought in the prior art that the optimum protective barrier thickness was one-half (½) or any multiple of one-half (½) of the wavelength of the transmitted pressure (energy). According to the prior art, at this thickness, the protective barrier material looks acoustically invisible and roughly twenty percent (20%) of the energy emitted from the transducers is being transmitted into the liquid beyond the protective barrier.

However, according to an embodiment of the present invention, it has been found that the transmission of energy through a material can be further optimized or enhanced if the thickness of that material, is between about 0.001 inches and about 0.125 inches, wherein the thickness is not n/2 of a wavelength of a transmitted pressure (energy) that is generated by the transducer(s) (10), wherein n is any integer. Without being limited to the mechanism, it is believed that roughly seventy percent (70%) of the energy emitted from the transducer(s) (10) may be transmitted into the liquid (30) beyond the protective barrier (60) with the thicknesses of the present invention, which is significantly higher than the 20% emitted from the protective barrier (60) with a prior art thickness of one-half (½) or any multiple of ½ the wavelength. Without being limited to the mechanism of action, the material of the protective barrier (60) may actually maximize the transmission coefficient of the pressure (energy) and thus increase the efficiency and effectiveness of the aerosol (200) output of the transducer(s) (10), in addition to protecting the electrode material. According to this embodiment, a preferred material of the protective barrier (60) may be glass, and more preferably quartz glass.

Based upon an embodiment, the invention gave rise to unexpected results, namely a significant increase in aerosol (200) output, smaller aerosol (200) particle size, and more energy being transferred to the liquid (30). Additionally, in an embodiment of the apparatus and methods of protecting a transducer(s) (10), a cooling system to prevent the transducer(s) (10) from burning or otherwise failing at various operating frequencies is not necessary. For example, U.S. Pat. No. 4,109,863, which is incorporated herein by reference in its entirety, including the references cited therein, requires a means for circulating a fluid over the transducer and glass for cooling and stabilizing a transducer. However, according to U.S. Pat. No. 4,976,259, this method has the undesirable effect of acoustically dampening the back side of the transducer which reduces the efficiency of the nebulizer system.

When calculating the optimum thickness of the protective barrier (60) in an embodiment of the present invention, the following are considered: (1) operating frequency; (2) the specific natural frequency of the transducer(s) (10); (3) the type of protective barrier (60) material; (4) the thickness of the protective barrier (60); (5) optionally, a suitable adhesive/bonding agent (70); and (6) an acceptable and optimum level of aerosol (200) by sweeping the transducer assembly (100) with a range of frequencies to find the desired aerosol (200) output.

According to an embodiment, once the transducer assembly (100) is assembled it can be operated at a range of frequencies. The thickness of the protective barrier (60) may range depending upon the operating frequency of the transducer(s) (10). According to an embodiment, the thickness of the protective barrier (60) ranges from about 0.001 inches to about 0.125 inches, wherein the thickness is not equal to n/2 of a wavelength of pressure (energy) generated by the transducer(s) (10) at a frequency between about 0.025 MHz and about 10 MHz, wherein n is any integer, preferably a thickness between about 0.026 inches and about 0.070 inches at a frequency between about 0.5 MHz and about 2.5 MHz, more preferably a thickness between about 0.030 inches and about 0.060 inches at a frequency between about 1.2 MHz and about 2.2 MHz, and even more preferably a thickness between about 0.029 inches and about 0.042 inches at a frequency between about 1.2 MHz and about 2.2 MHz. Unless otherwise stated, frequency in this specification refers to the operating frequency of the transducer(s) (10).

Empirical testing for hydrogen peroxide and peroxyacetic acid in solution; and water determined that the transducer(s) (10) generated the greatest amount of aerosol (200) when the liquid (30) above them was maintained at a temperature above about 80.degree. F., preferably about 105.degree. F. This is most likely due to the reduction of the surface tension of the liquid (30) as its temperature increases.

According to an embodiment, the liquid (30) may not have to be at least 80.degree. F. for effective performance in certain circumstances where high aerosol output is not necessary, or the liquid already has a low enough surface tension to achieve a desired result. Further, according to an embodiment, variations in the temperature may be made to optimize the aerosol (200) output based upon the type of liquid (30) used and the results desired by the user.

According to an embodiment, a protective barrier (60) for an aerosol (200) producing transducer(s) (10) has a thickness between about 0.001 inches and 0.125 inches, wherein the thickness is not n/2 of a wavelength of a transmitted pressure (energy) that is generated by the transducer(s) (10), wherein n is any integer. Thus, the thickness of the protective barrier (60) as described above permits the transducer(s) (10) to operate effectively to provide a high volume small aerosol (200) particle output, which is preferred, or any other desired output without the need for space between the transducer(s) (10) and the protective barrier (60) or a cooling mechanism.

According to an embodiment, many depths of the liquid (30) above the transducer(s) (10) may be used; preferably the depth of the liquid (30) above the transducer(s) (10) is from about 0.25 inches to about 8.0 inches, and more preferably a depth of about 1.25 inches. However, it may be possible to operate the invention at levels below 0.25 inches if lower power and/or frequencies are used. Moreover, according to an embodiment, the liquid (30) may be maintained at any temperature necessary to achieve the desired results based upon the preferences of the user or the type of liquid used. Preferably any liquid (30), such as peroxyacetic acid and hydrogen peroxide, in the reservoir (40) may be maintained at a temperature of about 80.degree. F. or greater in order to maximize the amount of aerosol (200) that is generated. However, the temperature of the liquid (30) may vary depending upon such parameters as the desired aerosol (200) output, the type of liquid (30) used, and the surface tension of the liquid (30).

Figure 6:
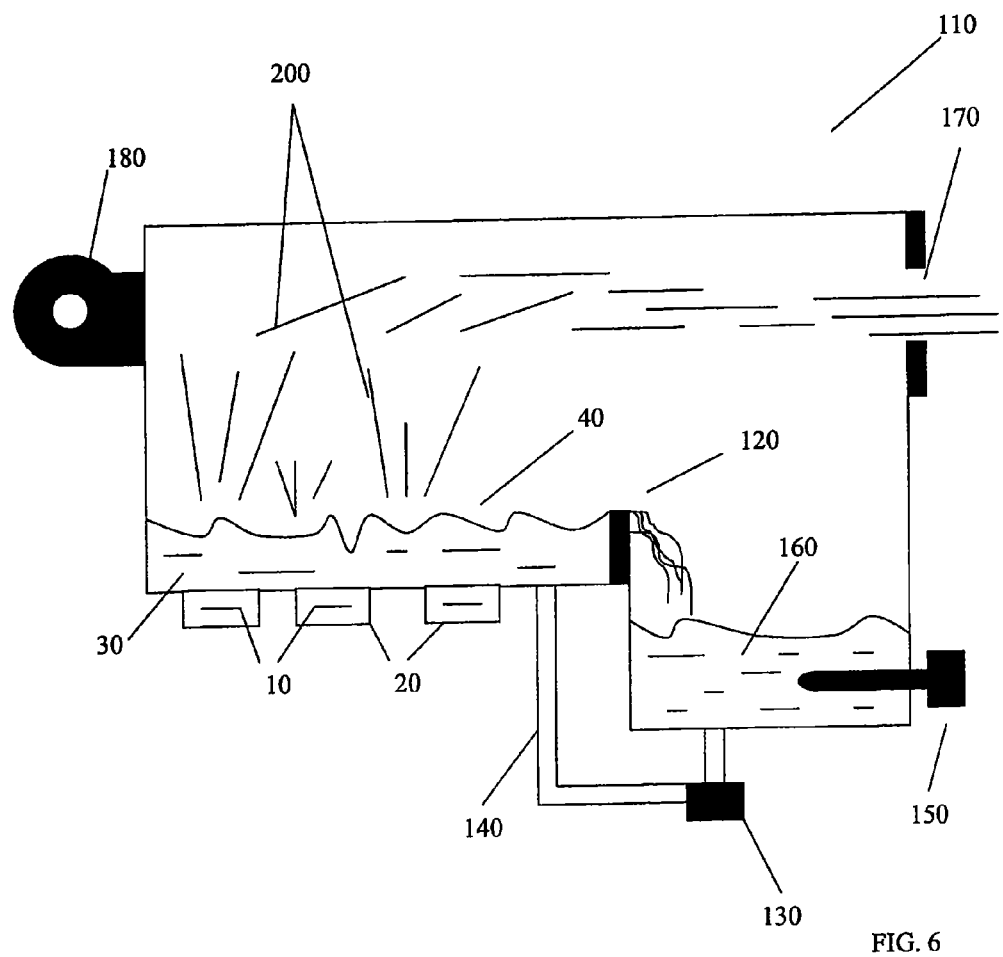
FIG. 6 is a schematic view of an embodiment of an aerosol generator according to the present invention.

Referring to FIG. 6, there is shown an embodiment of an aerosol generator (110) according to the present invention. The reservoir (40) contains a volume of liquid (30), the level of which is controlled by a dam (or weir gate) (120) operatively associated with a supply pump (130) and a supply line (140) to maintain the level of the liquid (30) at a preferred level above the transducer(s) (10) mounted on the bottom wall of the reservoir (40). The transducer(s) (10) may be individually mounted in separate housings (20), as shown in one of the embodiments of FIGS. 2-4, or they may all be coupled to a common protective barrier (60) wall and appropriately sealed from contact with the liquid (30). It has been found that efficiency of aerosol (200) generation is enhanced by heating the liquid (30) to at least 20.degree. F. above ambient, preferably to at least about 80.degree. F.; however the temperature may vary depending upon the type of liquid (30) used. A heater element (150) is coupled with a liquid supply sump (160) to control the temperature of the liquid (30). The aerosolized liquid (200) is delivered to the space to be treated via an exit orifice (170) of the aerosol generator (110) to which suitable piping (not shown) may be attached for delivery. A blower (180), fan, or other source of pressurized air generates the air flow necessary to deliver the aerosol (200), all in a manner well-known in the art.

However, in accordance with one aspect of the present invention, it has been found that the transmission of energy through a material can also be optimized if the thickness of that material, in this case glass, is one quarter (¼) or any multiple of one quarter (¼) of the wavelength of the transmitted pressure waves. The barrier material in this case will also look acoustically invisible and will maximize the transmission coefficient of the pressure waves and thus increase the efficiency and effectiveness of the transducer's aerosol output.

Testing was conducted in the laboratory to determine what glass thickness when adhered to the transducer would generate the maximum amount of aerosol. Transducers with an adhered quartz glass thickness of 0.096 inch and 0.125 inch were tested first, and both suffered damage when the heat from operating the transducer burned the epoxy, which is used to adhere the glass to the transducer. This was evidence that a thinner glass material was needed in order to more effectively impart the generated heat into the liquid above the glass. A quartz glass barrier of ¼ wave length of the propagated pressure wave or 0.036 inch was manufactured, and its output greatly exceeded the target of 800 milliliters of aerosolized liquid per hour with an average output of 1500 milliliters per hour. Thinner glass material would be impractical to implement due its propensity for breakage as well as increased difficulty to machine or process.

Further empirical testing in the laboratory determined that the actual optimum range of glass thickness for aerosol output was minus 0.010 inches and plus 0.024 inches, from 0.036 inches or the calculated optimum barrier thickness of one quarter (¼) of the wavelength of the transmitted pressure waves. It was also found that this asymmetrical range is strongly correlated with the admittance vs. frequency sweeps for transducers with glass barriers of this type. These sweeps show a sharp drop to the left of the initial curve's amplitude, and only a small drop on the right side of this same curve that then intersects with the amplitude of a second minor curve where the slope of this curve gradually tails off to the right. Finally, empirical testing determined that the transducers generated the greatest amount of aerosol when the liquid above them was maintained at a temperature above 80 degree Fahrenheit. This is most likely due to the reduction of the liquid's surface tension as its temperature increases.

Therefore, in the present invention the optimum glass barrier thickness for the aerosol producing transducer, is approximately one quarter (¼) or any multiple of one quarter (i.e.: ¼, ¾, 5/4 . . . or n/4 where n=any number or the result of any mathematical operation) of the wavelength of the transmitted pressure waves and within a range of minus 0.010 inches (−0.010 inches) and plus 0.024 inches (+0.024 inches) from the calculated optimum barrier thickness (0.036 inch). However, any multiple or resulting glass barrier thickness that mathematically results in one half (½) or a whole of a wavelength known in the prior art. The liquid depth above the transducers can range from 0.5 to 5.0 inches. In addition the liquid in the tank above the transducers should be maintained at a temperature of 80 degree Fahrenheit or greater in order to maximize the amount of aerosol that is generated. This method in its entirety can be used with any transducer with a natural resonant frequency, unloaded in air, between 0.5 MHz to 8.0 MHz.

Specifically, maximum aerosol output is achieved with a glass thickness within the range of minus 0.010 inches and plus 0.024 inches, from the optimum calculated glass barrier thickness of 0.036 inches (0.036−0.010 to 0.036+0.024 inches). In addition, the transducers have a natural resonant frequency, unloaded in air, between 1.25 to 1.65 MHz and their operating frequency range in liquid is between 1.71 to 2.00 MHz. Again, the liquid depth above the transducers can range from 0.5 to 5.0 inches, and its temperature is maintained above 80 degree Fahrenheit in order to maximize the amount of aerosol that is generated. Any deviation from these measurements and art results in severely diminished aerosol generation.

According to an embodiment, the transducer(s) (10) and the protective barrier (60) may be sized to provide an optimized resonant frequency that is operative when driven or operated at an operating frequency in the range of about 0.5 MHz to about 2.5 MHz. This large range is due to the appearance of two separate operating ranges that are apparently unique to the transducer assembly (100). For example, using a transducer(s) (10) having a resonant frequency of about 1.40 MHz to about 1.48 MHz with a protective barrier (60) thickness of about 0.036 inches, driven at an operating frequency ranging from about 1.78 MHz to about 1.98 MHz will most commonly show a maximized aerosol (200) output of at least about 1,000 ml per hour of the liquid (30). A second effective operating frequency with lower output is noted at about 1.2 MHz. According to an embodiment, for certain applications where the volume of the space to be treated is small, an output of at least 1,000 ml/hr may not be necessary. In such a situation, the transducer(s) (10) may be operated or driven with various combinations of power or volts peak to peak, and frequencies that result in the generation of lower aerosolized (200) liquid output. For example, in the treatment of a space the size of about a small glove box or the like, an output of 10 ml/hr or less may be adequate.

The apparatus and methods of the present invention may yield aerosol (200) droplets of various sizes. According to an embodiment, they may yield aerosol (200) droplets with a defined size distribution of mostly less than about one (1) microns in diameter, without being limited to a mechanism it is believed this allows the droplets to behave more like a gas with respect to Brownian movement and diffusion. The size of the aerosol (200) droplets may be adjusted according to the desired results. The small aerosol (200) droplet size enables the drops to penetrate small cracks and crevices, and apply very thin films on surfaces. In addition, the aerosol (200) may effectively reach and disinfect areas of contamination and areas of otherwise limited accessibility. Any means to create an aerosol (200) with droplets less than about 2-5 microns in size could be used in the present invention. Larger particles will by their nature cause less penetration and decrease the effectiveness. Thus, the present invention may generate predominantly submicron size droplets or sizes may be controlled for a desired result. According to an embodiment, the average particle size may range from less than one micron to about 10 microns, preferably less than about 5 microns, more preferably less than one micron, and even more preferably about 0.68 microns.

According to an embodiment, multiple transducer(s) (10) are typically used to provide an output volume of aerosolized liquid (200) sufficient to rapidly treat a large enclosed space. In such a case, the transducer(s) (10) may be mounted individually, or a plurality of transducer(s) (10) may be coupled to a single protective barrier (60), with one or more of the protective barrier (60) being coupled, mounted on or in a reservoir (40), or positioned within a reservoir (40) with an appropriate coupling device. Multiple transducer(s) (10) may be coupled to a single protective barrier (60) at varying distances apart, preferably between at least about 0.25 inches apart, more preferably about 0.75 inches apart.

EXAMPLE 1

To produce the transducer assembly, the protective barrier, in this case being glass, was first ground to a specified thickness and then adhered to the transducer using an adhesive. Pressure was then placed on the protective barrier for a period of time to aid adhesion of the protective barrier to the transducer.

EXAMPLE 2

The protective barrier was manufactured of a quartz glass with a thickness of between about 0.001 inches and about 0.125 inches, wherein the thickness is not n/2 of a wavelength (.lamda.) of a transmitted pressure (energy) that could be generated by the transducer(s), wherein n is any integer, or about 0.036 inches at an operating frequency between about 1.76 MHz to about 1.94 MHz. The aerosol output greatly exceeded the target of 800 milliliters of aerosolized liquid per hour with an average output of 1500 milliliters per hour. Thinner glass material may and has been used, but the thinner the glass is, the more difficult (or impractical) it is to implement due its propensity for breakage as well as increased difficulty to machine or process.

EXAMPLE 3

The effectiveness of various quartz glass barrier thicknesses was determined based upon various operating frequencies. Amplifier ENI-2100L and heater 600 W Watlow "firerod" were used. The temperature of the water solution, which was aerosolized, was heated to about 105.degree. F. Table 1 sets forth the results.

TABLE 1

| Frequency (Mhz) | Wavelength | Protective Barrier Thickness (inches) | Aerosol Results: Output Observations/Volumes (ml/hr) |
|---|---|---|---|
| 1.87 | 0.311 | 0.036 | 2138 ml per hr |
| 1.85 | 0.308 | 0.036 | 1769 ml per hr |
| 1.86 | 0.309 | 0.036 | 2064 ml per hr |
| 1.89 | 0.314 | 0.036 | 1622 ml per hr |
| 1.89 | 0.314 | 0.036 | 1843 ml per hr |
| 1.88 | 0.313 | 0.036 | 0 ml per hr; transducer burned |
| 1.90 | 0.316 | 0.036 | 1460 ml per hr |
| 1.84 | 0.306 | 0.036 | 1695 ml per hr |
| 1.85 | 0.308 | 0.036 | 1500 ml per hr |

TABLE 1-continued

| Frequency (Mhz) | Wavelength | Protective Barrier Thickness (inches) | Aerosol Results: Output Observations/Volumes (ml/hr) |
|---|---|---|---|
| 1.86 | 0.309 | 0.036 | 1825 ml per hr |
| 1.89 | 0.314 | 0.036 | 1870 ml per hr |
| 1.90 | 0.316 | 0.036 | 1550 ml per hr |
| 1.90 | 0.316 | 0.036 | 1550 ml per hr |
| 2.11 | 0.283 | 0.029 | Est. <500 ml per hr |
| 1.83 | 0.338 | 0.040 | 1971 ml per hr |
| 1.81 | 0.334 | 0.040 | 2138 ml per hr |
| 1.83 | 0.338 | 0.040 | 2005 ml per hr |
| 1.68 | 0.388 | 0.050 | 1769 ml per hr |
| 1.91 | 0.847 | 0.096 | 0 ml per hr; transducer burned |
| 1.58 | 0.912 | 0.125 | 0 ml per hr |
| 1.59 | 0.918 | 0.125 | 0 ml per hr |
| 1.88 | 0.313 | 0.036 | 0 ml per hr; transducer burned |
| 1.90 | 0.316 | 0.036 | 1900 ml per hr; amplifier issue - ran hot |
| 1.80 | 0.299 | 0.036 | 0 ml per hr; transducer burned |
| 1.82 | 0.303 | 0.036 | 0 ml per hr; lens may have been cracked |
| 1.71 | 0.355 | 0.045 | 0 ml per hr |
| 1.74 | 0.362 | 0.045 | 0 ml per hr |

High aerosol output was generated with varying protective barrier thickness at various operating frequencies. For example, a protective barrier with a thickness of 0.036 inches at an operating frequency of 1.87 MHz, and a protective barrier with a thickness of 0.040 at an operating frequency of 1.81 MHz, both generated 2138 ml per hour of aerosol.

For instances where the transducer burned, overheated, and/or otherwise failed (herein, collectively "failed"), the failure occurred within the first eight (8) hours of operation, but in other embodiments and situations, failure may also occur after eight (8) continuous or aggregate hours of operation. Additionally, in some circumstances failure of the transducer occurred within the first ten (10) minutes of operation, but in other embodiments and situations, failure may also occur after ten (10) continuous or aggregate minutes of operation.

EXAMPLE 4

The aerosol output for various liquid levels above a transducer was determined. The transducer had a natural frequency of 1.43 MHz, the protective barrier was quartz glass and had a thickness of 0.036 inches, the liquid was water, and the temperature of the water was 105.degree. F.-109.degree. F. Table 2 sets forth the findings.

TABLE 2

| LIQUID LEVEL (in inches) in Reservoir | AEROSOL OUTPUT (in ml/hour) |
|---|---|
| 8.0 | No aerosol |
| 7.25 | 1840 |
| 1.25 | 2218 |
| 0.875 | 2064 |
| 0.50 | 1769 |
| 0.40 | 1917 |
| 0.35 | Transducer burned |
| 0.175 | Transducer burned |

Liquid levels of 1.25 inches above the transducer resulted in the highest aerosol output at 2218 ml. At a liquid level of 0.35 inches and below, the transducer burned and at levels at about 8.0 inches, no aerosol was generated.

EXAMPLE 5

To determine the efficacy of the apparatus and methods of an embodiment of the present invention, a solution comprising approximately 1% hydrogen peroxide and approximately 0.25% peroxyacetic acid was tested on certain biological indicators. The transducer had a natural frequency of 1.83 MHz and a glass protective barrier with a thickness of 0.036 inches. The solution was heated to 105.degree. F. The indicators were manufactured utilizing paper filter strips inoculated with bacterial spores of either *Geobacillus stearothermophilus* ATCC #12980, or *Bacillus atrophaeus* ATCC #9372. Initial assays were performed and populations on all three substrates were a minimum of 1.0.times.10.sup.6.

Samples of the inoculated filter paper were placed in a sealed Plexiglas chamber measuring 8'.times.4'.times.5' to which an aerosolized aqueous hydrogen peroxide and peroxyacetic acid cloud, generated in an apparatus similar to that shown in FIG. 6, was applied for approximately five (5), twelve (12), and seventeen (17) minutes, of which the inoculated filter paper was completely exposed to the aerosol for at least three (3), at least ten (10), and at least fifteen (15) minutes, respectively. The samples were kept in the sealed chamber for approximately twenty-two (22) additional minutes before the room was ventilated.

A. Culturing Results for *Bacillus atrophaeus* ATCC #9372:

Chamber air temperature before the test was approximately 76.degree. F. and the disinfectant temperature was approximately 104.degree. F. The samples were incubated at 30-35.degree. C. for seven (7) days. Positive Control showed growth as expected.

| Time (in minutes) | Location* | Sample No.** | Observation |
| --- | --- | --- | --- |
| 3 | Top | A | No Growth |
| 3 | Top | B | No Growth |
| 3 | Top | C | No Growth |
| 3 | Bottom | A | No Growth |
| 3 | Bottom | B | No Growth |
| 3 | Bottom | C | No Growth |
| 10 | Top | A | No Growth |
| 10 | Top | B | No Growth |
| 10 | Top | C | No Growth |
| 10 | Bottom | A | No Growth |
| 10 | Bottom | B | No Growth |
| 10 | Bottom | C | No Growth |
| 15 | Top | A | No Growth |
| 15 | Top | B | No Growth |
| 15 | Top | C | No Growth |
| 15 | Bottom | A | No Growth |
| 15 | Bottom | B | No Growth |
| 15 | Bottom | C | No Growth |

*"Top" denotes samples attached to wire strung approximately 51 inches above the chamber floor. "Bottom" denotes samples attached to a wire strung approximately 22 inches above the chamber floor.
**Each location had three (3) separate test strips A-C for each time frame.

B. Culturing Results for *Geobacillus stearothermophilus* ATCC #12980:

Chamber air temperature before the test was approximately 76.degree. F. and the disinfectant temperature was approximately 104.degree. F. The samples were incubated at 55-60.degree. C. for seven (7) days.

| Time (in minutes) | Location | Sample No. | Observation |
| --- | --- | --- | --- |
| 3 | Top | A | No Growth |
| 3 | Top | B | No Growth |
| 3 | Top | C | No Growth |
| 3 | Bottom | A | No Growth |
| 3 | Bottom | B | No Growth |
| 3 | Bottom | C | No Growth |
| 10 | Top | A | No Growth |
| 10 | Top | B | No Growth |
| 10 | Top | C | No Growth |
| 10 | Bottom | A | No Growth |
| 10 | Bottom | B | No Growth |
| 10 | Bottom | C | No Growth |
| 15 | Top | A | No Growth |
| 15 | Top | B | No Growth |
| 15 | Top | C | No Growth |
| 15 | Bottom | A | No Growth |
| 15 | Bottom | B | No Growth |
| 15 | Bottom | C | No Growth |

Although the present invention has been described in terms of specific embodiments, changes and modifications can be carried out without departing from the scope of the invention which is intended to be limited only by the scope of the claims.

We claim:

1. An apparatus for optimizing aerosol generation, comprising:
   at least one transducer;
   a fluid reservoir containing a liquid, an aerosol is generated from the liquid; and
   a protective barrier secured to the at least one transducer, the protective barrier being fabricated from a material which protects the at least one transducer from a chemical interaction with the liquid, the protective barrier is in direct contact with the liquid, wherein the protective barrier has a thickness of between 0.001 inches and 0.125 inches that is approximately n/4 of a wavelength of a wave generated by the at least one transducer at a resonant frequency for the at least one transducer, wherein n is any odd integer, and wherein the at least one transducer is operated at an operational frequency that is different than the resonant frequency to produce the aerosol.

2. The apparatus of claim 1 wherein the protective barrier has a thickness of between about 0.036 inches and 0.050 inches.

3. The apparatus of claim 1 wherein the protective barrier has a thickness of between about 0.026 inches and 0.060 inches.

4. An apparatus for optimizing aerosol generation, comprising:
   at least one transducer including a conductive layer;
   a fluid reservoir containing a liquid, an aerosol is generated from the liquid; and
   a protective barrier being bonded to the conductive layer, the protective barrier is in direct contact with the liquid, the protective barrier being fabricated from a material which protects the at least one transducer from at least one of an acid and alkaline, wherein the protective barrier has a thickness that is approximately n/4 of a wavelength of a wave generated by the at least one transducer at a resonant frequency between about 0.025 MHz and about 10 MHz for the at least one transducer, wherein n is any odd integer, and wherein the at least one transducer is operated at an operational frequency that is different than the resonant frequency to produce the aerosol.

5. The apparatus of claim 4 wherein the resonant frequency is between about 0.050 MHz and 8.0 MHz.

6. The apparatus of claim 4 wherein the resonant frequency is between about 0.050 MHZ to about 2.5 MHz.

7. The apparatus of claim 4 wherein the resonant frequency is between about 1.25 MHz to about 1.65 MHz.

8. The apparatus of claim 7 wherein the transducer has an operating frequency of between about 1.71 MHz to about 2.00 MHz.

9. The apparatus of claim 7 wherein the transducer has an operating frequency of between about 1.76 MHz to about 1.94 MHz.

10. The apparatus of claim 4 wherein the resonant frequency is between about 1.40 MHz to about 1.48 MHz.

11. The apparatus of claim 10 wherein the transducer has a primary operating frequency of between about 1.78 MHz to about 1.98 MHz.

12. The apparatus of claim 11 wherein the transducer has a secondary operating frequency of about 1.2 MHz.

13. The apparatus of claim 1 wherein the protective barrier is bonded to the at least one transducer.

14. The apparatus of claim 1 wherein the transducer is powered with an operating voltage between 100-300 volts.

15. An apparatus for optimizing aerosol generation, comprising:
   a) at least one transducer including a conductive layer,
      a fluid reservoir containing a liquid, an aerosol is generated from the liquid; and
   b) a protective barrier being bonded to the conductive layer with a bonding substance, said bonding substance is disposed between said transducer and said conductive layer, the protective barrier is in direct contact with the liquid, wherein the protective barrier has a thickness of between 0.001 inches and 0.125 inches that is approximately n/4 of a wavelength of a wave generated by the at least one transducer at a resonant frequency for the at least one transducer, wherein n is any odd integer, and wherein the at least one transducer is operated at an operational frequency that is different than the resonant frequency to produce the aerosol.

16. The apparatus of claim 15 wherein the protective barrier has a thickness of between about 0.036 inches and 0.050 inches.

17. The apparatus of claim 15 wherein the protective barrier has a thickness of between about 0.026 inches and 0.060 inches.

18. The apparatus of claim 15 wherein the at least one transducer is operated between 20-300 volts.

* * * * *